(12) United States Patent
Lawrence et al.

(10) Patent No.: US 6,224,905 B1
(45) Date of Patent: *May 1, 2001

(54) BICONVEX RAPIDLY DISINTEGRATING DOSAGE FORMS

(75) Inventors: Janice Lawrence, Gregory; Gary Posage, Rochester Hills, both of MI (US)

(73) Assignee: Janssen Pharmaceutica N.V. (BE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/194,808
(22) PCT Filed: Jun. 10, 1997
(86) PCT No.: PCT/EP97/03065
  § 371 Date: Dec. 3, 1998
  § 102(e) Date: Dec. 3, 1998
(87) PCT Pub. No.: WO97/48383
  PCT Pub. Date: Dec. 24, 1997

Related U.S. Application Data
(60) Provisional application No. 60/020,259, filed on Jun. 17, 1996.

(51) Int. Cl.[7] .................................................. A61K 9/20
(52) U.S. Cl. ...................... 424/464; 424/465; 424/485; 424/486; 424/488; 424/439; 424/441; 514/770; 514/772.3; 514/773; 514/774; 514/776; 514/777; 514/779; 514/780; 514/781; 514/782; 514/783
(58) Field of Search ................................... 424/484, 464, 424/465, 485, 486, 488, 439, 441

(56) References Cited

U.S. PATENT DOCUMENTS

| | | | |
|---|---|---|---|
| 4,758,598 | 7/1988 | Gregory | 514/774 |
| 4,792,448 | 12/1988 | Ranade | 424/428 |
| 5,516,530 | 5/1996 | Lo et al. | 424/473 |

FOREIGN PATENT DOCUMENTS

| | | |
|---|---|---|
| 2 111 423 | 7/1983 | (GB) . |
| 93/23017 | 11/1993 | (WO) . |
| 95/09608 | 4/1995 | (WO) . |

Primary Examiner—James M. Spear
(74) Attorney, Agent, or Firm—Ellen Ciambrone Coletti

(57) ABSTRACT

A method for preparing solid rapidly disintegrating dosage forms shaped as biconvex tablets having symmetrical top and bottom surfaces and dosage forms obtainable thereby.

23 Claims, 4 Drawing Sheets

BICONVEX RAPIDLY DISINTEGRATING DOSAGE FORMS

CROSS REFERENCE TO RELATED APPLICATIONS

This application is the national stage of application no. PCT/EP97/03065, filed on Jun. 10, 1997, which application claims priority from U.S. Ser. No. 60/020,259, filed Jun. 17, 1996.

The present invention relates to a process of preparing solid rapidly disintegrating dosage forms shaped as a biconvex tablets having symmetrical top and bottom surfaces, and to dosage forms obtainable thereby.

Solid rapidly disintegrating dosage forms loaded with a predetermined quantity of an active ingredient are known from GB-A-1,548,022 (U.S. Pat. No. 4,305,502). These solid dosage forms comprise a porous network of a matrix material carrying an active ingredient, the matrix material consisting of a water-soluble or a water-dispersable carrier material. The solid dosage forms are prepared by freeze-drying or lyophilization of the solvent from a frozen solution or suspension of the matrix material and the active ingredient.

Various improvements for preparing dosage forms by lyophilization have been developed. GB-A-2,111,423 and U.S. Pat. No. 4,371,516 disclose such methods of preparing solid dosage forms which are rapidly disintegrated by water and in which a network of matrix material carries a predetermined amount of an active ingredient, particularly a pharmaceutical substance. Such dosage forms find many applications, particularly where it is desired to administer, dispense or otherwise utilise an active ingredient in predetermined unit quantities. For example, certain active ingredients which are used in solution or suspension form, but which are difficult or hazardous to transport or store in such form, may be converted into a solid form which can be added by the user to an aqueous medium to produce the desired solution or dispersion containing a predetermined amount of the active ingredient. Further, the active ingredient may be a reagent which can be added to a known amount of aqueous liquid to produce a standardised liquid composition which then can be used, for example, in chemical analysis. Further, the active ingredient may be a diagnostic compound which has to be added to a biological sample (e.g. blood, urine) and thus allows one to determine the amount of a particular constituent present in the sample. Preferably, however, the active ingredient is a drug substance for human or veterinary use. Rapidly dissolving solid drug dosage forms are particularly suitable for oral administration. When orally administered they generally disintegrate rapidly in the mouth (e.g. within one or two seconds) and thus the dosage form is a particularly advantageous means for administering drugs to humans and animals. Such dosage forms can be used as alternatives to conventional tablets, pills or capsules, particularly for patients—humans and animals alike—who have difficulty in swallowing these conventional dosage forms. U.S. Pat. No. 4,642,903 teaches a procedure for preparing a freeze-dried foam dosage form using conventional lyophilization techniques which results in rapidly dissolving pharmaceutical dosage forms.

WO-93/23017 addresses a problem intrinsic to conventional lyophilization methods, namely the lack of uniform porosity in the lyophilized product. Uniform porosity in a lyophilized product is critical for post-loading a placebo or unloaded dosage form with an active ingredient. WO-93123017 concerns a method of producing a dosage form that will avoid cracking and meltback, has adequate strength, and porosity and exhibits a fast speed of dissolution.

Other methods for the preparation of solid dosage forms which rapidly disintegrate in the mouth, namely solid state dissolution techniques are disclosed in U.S. Pat. No. 5,039,540, U.S. Pat. No. 5,215,756, U.S. Pat. No. 5,330,764. and U.S. Pat. No. 5.298,261.

GB-2,119,246 concerns a process of preparing solid dosage forms using molds having a side wall or walls diverging outwardly from the base and making an angle of at least 5° at the surface of the composition. When lyophilizing underfilled molds of this type, one obtains solid shaped articles which have a more even thickness and thus are flatter than articles obtained from underfilled molds with side walls perpendicular to the base.

Solid dosage forms as provided by the prior art are used to deliver predetermined amounts of active ingredients. Since the administration of such products is associated with many risks, there is a need to package them adequately, e.g. in blister packs, and to bestow an identity on them.

The packaging of solid rapidly disintegrating dosage forms prepared according to prior art methods, especially on a large industrial scale, is associated with a number of particular problems. First, the friability of such dosage forms seriously constrains the methods by which they can be transported and handled. Consequently, any reduction in the friability of solid rapidly disintegrating dosage forms will greatly enhance their industrial utility by relaxing the production constraints. A second problem which directly relates to the shape of solid rapidly disintegrating dosage forms prepared according to prior art methods concerns the fact that the top and bottom surfaces of the dosage forms often are not symmetrical. Usually the bottom will be a flat surface more or less perpendicular to the side wall or walls of the dosage form, whereas the top surface may be concave or flat, depending upon the extent to which the molds are filled. Dosage forms in which top and bottom are distinct have the disadvantage that they may call for process steps to orient the dosage forms prior to filling them in blister packs (the process involves detecting each individual form's orientation, and selecting and reversing those forms that have the undesired orientation).

The present invention provides a single solution to all these problems, consisting of imparting a symmetrical convex top and bottom surface to solid rapidly disintegrating dosage forms. First, this results in dosage forms with less acute angles between side wall or walls and top or bottom surfaces which reduces the friability of the dosage forms. The symmetry further means that there is not any longer a distinction between bottom and top of a dosage form once it is removed from its mold. The biconvex shape has the further advantage that the dosage forms can easily be arranged to lie on one of their convex surfaces by gently shaking them. In addition, they can easily be picked up, either during production and packaging, or later by the patient or the person administering the dosage form.

The biconvex shape of the solid dosage forms prepared according to the present invention also serves to distinguish them from other prior art dosage forms and thus may assist in preventing errors by physicians, pharmacists or by the end-users, the patients in the administration of medicines loaded onto biconvex-shaped dosage forms.

Figure 1:
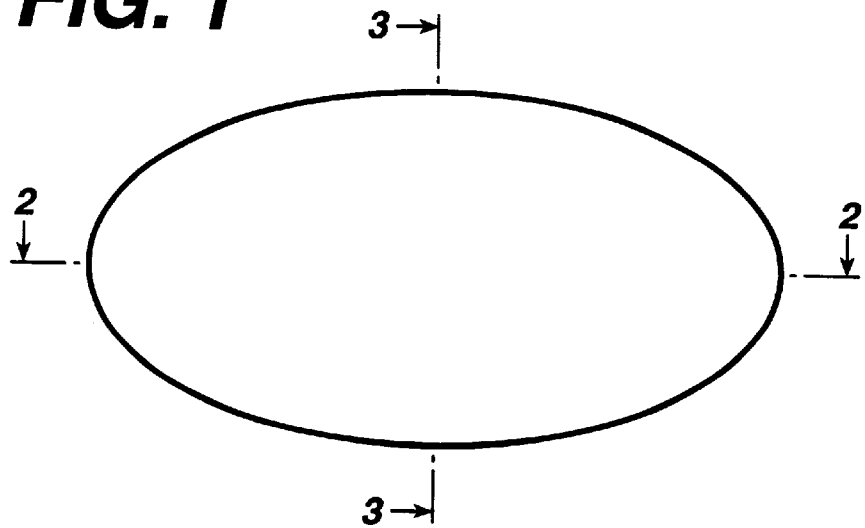
FIG. 1 shows an oval (elliptical) mold of 0.5 ml (scale 5:1) viewed from above
Figure 2:
FIGS. 2 and 3 show two cross sections of the mold of FIG. 1.
Figure 3:

The present invention is concerned with a process for the preparation of a solid rapidly disintegrating dosage form comprising a porous network of matrix forming materials, which process comprises:

overfilling a mold with a predetermined amount of an aqueous composition comprising the matrix forming materials so that a convex meniscus is created on top of the mold;

freezing the aqueous composition in the mold; and removing the solvent from the frozen composition by subjecting it to lyophilization or to solid state dissolution, thus leaving a porous network of matrix forming materials;

characterized in that the shape of the bottom surface of the mold is a mirror-image of the shape of the frozen meniscus on the top, the mirror-plane being parallel to the plane defined by the rim of the mold, thus yielding a dosage form shaped as a biconvex tablet having symmetrical top and bottom surfaces.

The aqueous compositions may be frozen by any conventional cooling process. For example, the aqueous compositions may be frozen by dispensing it into preformed molds corresponding to the size and shape of the desired dosage form and subsequently cooling such molds on refrigerated shelves or in refrigerated chambers. Alternatively, the molds containing the mixture may be passed through a stream of cold gas or vapor, such as liquid nitrogen in a freezing tunnel. In a preferred method of freezing, the composition is passed through a freezing tunnel into which liquid nitrogen is injected, the liquid nitrogen being vaporised and the resulting cold gaseous nitrogen being passed over the composition. Another method for freezing the aqueous compositions in the molds is to surround the molds in dry ice until the aqueous composition is frozen.

The best-known process of removing solvents from frozen solutions or dispersions is lyophilization which involves desolvation of the mixture by sublimation of the solvent under a vacuum. If desired, the frozen compositions may be stored in a cold store before the sublimation process is carried out. The sublimation may be carried out in a freeze drier by subjecting the frozen composition in the mold to reduced pressure and, if desired, controlled application of heat to aid the sublimation. The pressure can be below 4 mmHg (533 Pa), e.g. below 0.3 mmHg (40 Pa), for example 0.1 to 0.2 mmHg (13.3 to 26.6 Pa) or even below 0.05 mmHg (6.7 Pa). The initial temperature in the freeze drier may be, for example, as high as 60° C. and this temperature can be reduced (e.g. to 40° C.) as the temperature of the frozen composition increases. Various methods and improvements are described in the references cited at the very beginning of the specification. The frozen compositions also may be removed from the mold prior to lyophilization.

The dosage forms can also be prepared by a solid-state dissolution method of removing solid solvent from frozen samples. In this less conventional method, one or more matrix forming agents are dissolved or dispersed in a first solvent, frozen and subsequently contacted with a second solvent at a temperature at or higher than the solidification point of the second solvent and at a temperature at or lower than the solidification point of the first solvent. The first solvent in the solidified state is substantially miscible with the second solvent, while the matrix forming agent(s) are substantially insoluble in the second solvent. The first solvent is thereby substantially removed from the solidified matrix yielding a solid matrix substantially free of the first solvent. Typically, the first solvent is water and the second ethanol.

The biconvex dosage forms obtainable by the processes according to the present invention can be prepared in a variety of sizes. The volume of the mold is conveniently in the range of 300 to 2,000 mm$^3$ (0.3 to 2 ml) and the volume of the dosage form is in the range of 350 to 2,500 mm$^3$ (0.35 to 2.5 ml). Preferably, the volume of the mold is in the range of 350 to 800 mm$^3$ (0.35 to 0.8 ml) and the volume of the dosage form is in the range of 450 to 1,000 mm$^3$ (0.45 to 1 ml). In other words, the overfill or the volume of the convex meniscus above the mold can be up to 30% of the volume of the mold itself. Generally speaking said overfill will be in the range of from 20% to about 26% of the volume of the mold. Besides the extent of the overfill, the size of the convex meniscus is constrained by the contact angle between the aqueous composition and the material forming the rim of the mold and the surface tension of the aqueous composition. It is important to note that the larger the overfill is, the greater the curvature of the convex surface will be. This, in turn maximizes both the reduction in friability and the improvement of the handling properties.

The maximum depth of the mold is conveniently in the range of 3.4 to 6 mm; or the maximum thickness of the frozen composition in the mold is in the range of 5.0 to 8.5 mm. This maximum distance is the distance measured along the axis perpendicular to the rim of the mold and running through the upmost point of the meniscus on the top of the mold and the downmost point on the bottom of the mold. Lower values are generally not preferred because the resulting dosage forms are so thin that their strength is often insufficient, whereas larger values for the thickness are often undesirable because of the difficulty in effectively removing all solvent from such frozen compositions, especially when using lyophilization for removing the solvent.

The area of the surface defined by the rim of the mold is typically in the range of 100 to 500 mm$^2$ and has a rounded shape. The rounded shape contributes to the mechanical strength of the dosage form by reducing its friability. Said rounded shape can be circular, elliptical, oblong, oblate or polygonal, the latter preferably with rounded corners if the internal angle[2] 90°.

The mold can be, for example a depression in a metal plate (e.g. an aluminium plate). The plate may contain more than one depression, each depression being of the size and shape corresponding to the desired size of the shaped article. However, the mold may also be a depression in a sheet of filmic material. The filmic material may contain more than one depression. The filmic material may be similar to that employed in conventional blister packs which are used for packaging pharmaceutical tablets and the like medicament forms. For example, the filmic material may be made of thermoplastic material with the depressions formed by thermo-forming. The preferred filmic material is a talc-filled polypropylene film or a polyvinyl chloride film. Laminates of filmic material such as polyvinyl chloride/polyvinylidene chloride, polyvinyl chloride/poly-tetrafluorethylene or polyvinyl chloride/polyvinylidene chloride/polyethylene may also be used.

Where lyophilization is used, it may be advantageous to freeze the matrix material solution in molds that are coated or lined for easy release of the frozen material. Preferred molds are thermoformed cups made in talc-filled polypropylene sheets, optionally siliconized with a layer of silicone/simethicone baked on the surface(s) which come into contact with the aqueous composition.

The profile and volume of the bottom of the mold can be determined as described hereunder. A first mold having the desired volume and having a flat bottom (parallel to the rim of the mold) with the desired rounded shape is overfilled to the desired extent with the aqueous solution from which the final dosage form is to be prepared. This is processed to a dosage form by freezing and removing the solvent. The volume of the meniscus can be determined by substracting the mold volume from the volume added to the mold, or alternatively by calculating the volume from a number of equations describing the top surface of the meniscus. One such way comprises sectioning the dosage form along one or more symmetry planes, measuring the cross section where said symmetry plane intersects the top surface of the meniscus and determining the equation describing said intersection. As one can safely assume that an ellipse adequately describes such intersections, measurement of the major axis and minor axis readily provides the parameters required for each equation. The equations of the intersections of the top surface of the meniscus with the various symmetry planes (along which the cross sections were made) can then be used to derive the equation describing the top surface of the meniscus, and using art-known integration methods, the volume of the meniscus can then be calculated. With the thus obtained information one can then proceed to calculate how the mold needs to be reshaped in order to yield a biconvex symmetrical dosage form. For example, one can calculate to which extent the depth of the original mold needs to be reduced so that the volume of the mold is reduced by the volume of the meniscus, followed by adding the mirror image of the top meniscus at the bottom of the mold. This procedure secures that the convex bottom has both the shape and the volume of the meniscus on the top which will eventually be used. The data obtained in the calculations are then provided to the manufacturer of the mold so that the convex shaped mold can be shaped in metal.

The aqueous composition may be in a variety of forms such as a solution, a suspension, a dispersion, an emulsion, or a foam. Persons skilled in the art will recognize acceptable methods for preparing each of these. Water is preferably employed as the solvent in the composition which is frozen and desolvated. An additional co-solvent (such as an alcohol) may also be used if it is desired to improve the solubility, dispersability or wettability of any of the ingredients of the composition.

The dosage form comprises a porous network of matrix forming materials comprising:
i) a water-soluble, hydratable gel or foam-forming material,
ii) a rigidifying agent for the gel or foam-forming material, and optionally
iii) one or more amino acids.

Suitable water-soluble, hydratable gel or foam-forming materials include proteinaceous materials such as gelatin, gelatin A, gelatin B, fluid gelatin, modified fluid gelatin, gelatin derivatives, albumin, soy fiber protein, wheat and psyllium seed proteins, potato protein, papain; phospholipids such as coacervate egg lecithin, or lecithin; gums such as acacia, guar, agar, locust bean, xanthan and tragacanth gum; polysaccharides such as alginates, polymannuronic acid, chitosan, carrageenans, dextrans, dextrins, maltrins (maltodextrins), pectins, polygalacturonic acid, microcrystalline cellulose, corn syrup solids, konjac flour, rice flour, wheat gluten; synthetic polymers such as polyvinylpyrrolidone, sodium carboxymethyl-cellulose, sodium starch glycolate, hydroxyethylcellulose; and polypeptide/protein or polysaccharide complexes such as gelatin-acacia complexes, each singly or in combination.

Suitable rigidifying agents include monosaccharides, linear and cyclic oligosaccharides and polysaccharides, e.g. mannitol, xylitol, sorbitol, dextrose, fructose, sucrose, lactose, maltose, galactose, trehalose; cyclic sugars such as cyclodextrins e.g. beta-cyclodextrin and 2-hydroxypropyl-beta-cyclodextrin; dextran, dextrin; and further include inorganic substances such as sodium phosphate, sodium chloride, magnesium aluminum silicates, magnesium trisilicate, natural clays, or a combination thereof. The preferred rigidifying agent is mannitol.

Suitable amino acids have from 2 to 12 carbon atoms, e.g. glycine, L-alanine, L-aspartic acid, L-glutamic acid, L-hydroxyproline, L-isoleucine, L-leucine, L-phenylalanine, or a combination thereof. Glycine is the preferred amino acid. Dosage forms containing glycine as one of the matrix forming components have several advantages: quick dissolution and disintegration in aqueous media, pleasant taste and mouthfeel, nutritional value, low caloric content and noncariogenicity. Of particular importance is the fact that these dosage forms can be produced with minimal cracking or meltback and that they have uniform porosity and adequate strength of handling, i.e. resistance to disintegration or crumbling under normal manufacturing and handling conditions. These latter properties contribute to the feasibility of the post-loading processes whereby active ingredients are loaded onto placebo or unloaded dosage forms.

Preferred matrix forming agents include pharmaceutical grade gelatins, pectins (non-hydrolyzed, partially hydrolyzed or hydrolyzed), glycine and mannitol. A particularly preferred combination of matrix forming agents comprises gelatin, glycine and mannitol.

The percentages and ratios mentioned in the following paragraphs are all by weight.

The solution or dispersion of materials for preparing the matrix can contain from 0.1% to 15% by weight of gel or foam forming material, in particular from 1% to 5% more in particular from 1.2% to 3%. It can further contain from 0.5% to 10%, in particular from 0.8% to 2.5% by weight of amino acid and from 0.5% to 10%, in particular from 1% to 4% of rigidifying agent, the remainder being solvent and secondary components as mentioned hereinafter.

The ratios between these materials may vary within certain ranges. In particular the weight by weight ratio of the total amount of amino acids to that of the water-soluble, hydratable gel or foam-forming material is from 1:1 to 1:3. A preferred ratio is 1.5: 1. The weight by weight ratio of the amount of the water-soluble, hydratable gel or foam-forming material to that of the rigidifying agent is from 2:1 to 1:2. A preferred ratio is 1.5:2.

Typically, the weight by weight ratio of the total amount of non-solvent components to that of the water in the aqueous composition is in the range of about 1:9 to 1:33, in particular from about 1:13 to 1:30, for example about 1:20.

Solid rapidly dissolving dosage forms find many applications, particularly where it is desired to administer, dispense or otherwise utilise an active ingredient in predetermined unit quantities. The active ingredient in particular is a drug substance for human of veterinary use.

The active ingredient used in the solid rapidly dissolving dosage form may be present in a coated form. For example, it may be present in particulate form and the particles of the active ingredient may be coated with an appropriate coating agent so as to protect it from process diluents, the aqueous environment of the suspension or of the oral or other mucosal cavity. or other environmental conditions that would dissolve or deteriorate said active ingredient. These coating materials may be selected from natural or synthetic polymers that are either hydrophilic or hydrophobic in nature or other hydrophobic materials such a fatty acid, glycerides, triglycerides and mixtures thereof. In this way, the taste of the active or bioactive agent may be masked, while at the same time permitting the solid dosage form to dissolve rapidly upon contact with physio-logical diluents. Examples of bitter active ingredients that may be coated in accordance with the present invention include acetaminophen. ibuprofen, chlorpheniramine maleate, pseudoephedrine, dextromethorphan, cisapride, domperidone, risperidone. Pharmaceutical applications comprise dosage forms having mucoadhesive properties or designed to deliver a drug at a controlled rate; dosing units designed to deliver drugs in the eye, in vaginal, rectal and other body orifices; solid dosage forms designed to replace liquid formulations; dry medicated preparations for topical application after resolution (reconstitution); preparation of medicated units or sheets for topical application; preparation of more palatable dosage forms of drugs that exhibit disagreeable organoleptic properties; dosage forms for oral delivery of drugs to persons who have difficulty swallowing tablets or capsules.

Secondary components such as nutrients, vitamins, other active ingredients, sweeteners, flavouring agents, colouring agents, surfactants, preservatives, antioxidants, viscosity enhancers, minerals, diagnostics, fertilizers and insecticides may also be incorporated in the formulation of the dosage form.

The solution or suspension of which the dosage forms are made may further contain the secondary components mentioned before. Xanthan gum or polyacrylic acid polymers and salts thereof (also referred to as carbomers or carboxyvinyl polymers, e.g. Carbopol™) may be added in order to increase viscosity, or to keep the components of the mixture in suspension.

The present invention also provides biconvex, solid rapidly disintegrating dosage forms obtainable by any one of the processes described hereinbefore.

The speed with which the biconvex tablet prepared by the inventive method dis-integrates is dependent entirely or at least in large part on the choice of matrix forming agent(s), their concentration and the solidification/desolvation process conditions. In particular, dosage forms of the size mentioned in the examples described hereinafter, will dissolve or disperse rapidly, for example, in less than about 10 seconds and generally faster e.g. in less than about 5 or even less, e.g. within 1 to 2 seconds.

The dosage forms disperse rapidly in water, e.g. in less than 10 seconds. The disintegration time of a dosage form is determined to check whether it is capable of being disintegrated by water sufficiently rapidly using a standard tablet disintegration apparatus as described in British Pharmacopoeia, 1980, Vol II, Appendix XII A, but with the standard 2.00 mm wire mesh replaced by stainless steel 40 mesh screen. A sample product is placed in a dry tube held above the surface of the water. The apparatus is started and the sample immersed in water at 20° C. The sample should disperse on the liquid surface and any solid residue should pass through the 40 mesh screen within 10 seconds, preferably within 5 and ideally within 1 to 2 seconds.

The invention is illustrated further by the following examples wherein the active ingredients are pharmaceuticals. It is to be understood that the methods according to the present invention and the dosage forms thereby obtainable are applicable to many other types of active ingredients.

Experimental part

A number of essential parameters defining convex molds according to the present invention are shown in the following Table 1. The following parameters are listed $V_t$: volume of the dosage form $S_c$: surface defined by the rim of the mold $H_c$: height of the side wall of the mold which is perpendicular to $S_c$ $H_m$: height of the meniscus (also the depth of the convex bottom of the mold)

$H_t$: total height of the dosage form=Hc+2 Hm

Curve 1 (2): values of the major and minor axes defining the elliptical curve which describes the intersection of the top surface of the meniscus with a first (second) intersecting cross section along one of the symmetry planes $V_c$: volume of part of the mold given by Sc×Hc Vm: volume of meniscus or of convex bottom of the mold given by (Vt−Vc)/2

Figure 4:
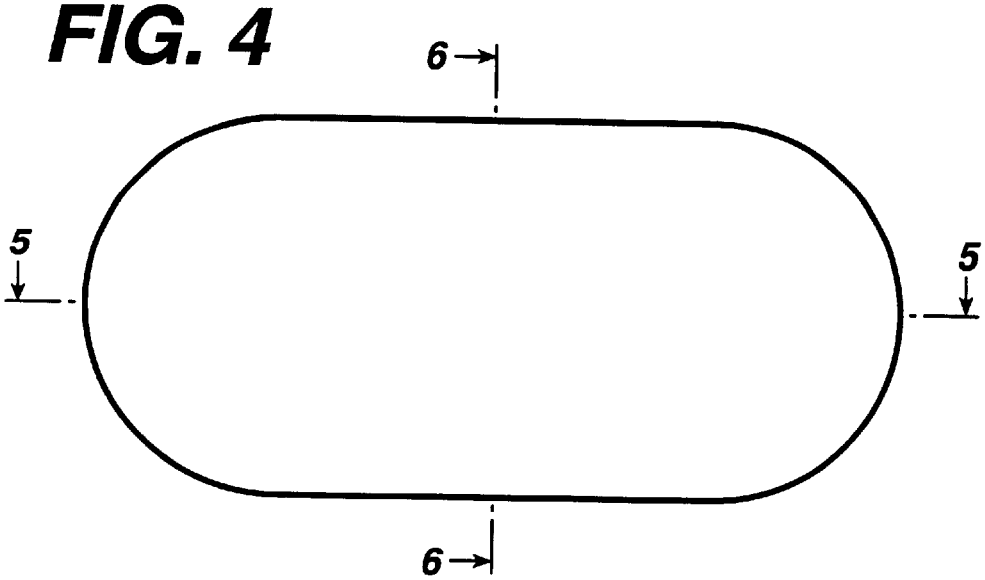
FIG. 4 shows a caplet (oblate) mold of 1.0 ml (scale 5:1) viewed from above
Figure 5:
FIGS. 5 and 6 show two cross sections of the mold of FIG. 4.
Figure 6:
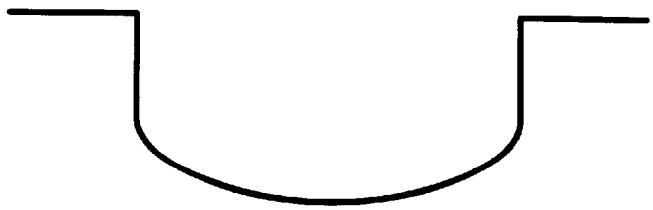
Figure 7:
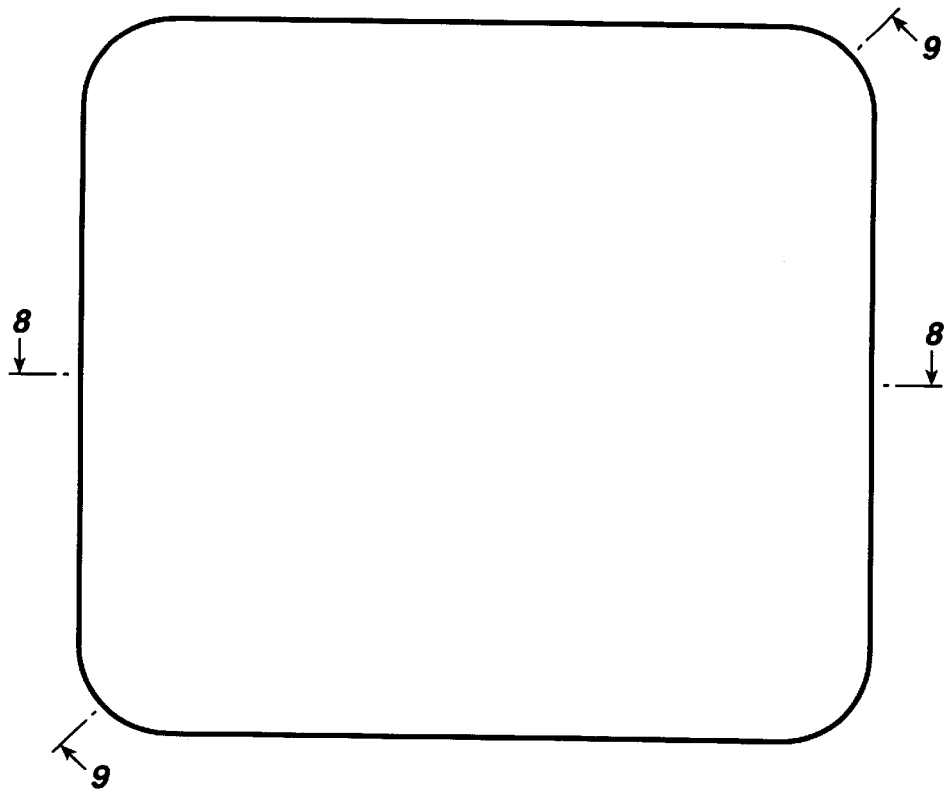
FIG. 7 shows a square mold with rounded corners of 0.5 ml (scale 5:1) viewed from above
Figure 8:
FIGS. 8 and 9 show two cross sections of said mold.
Figure 9:
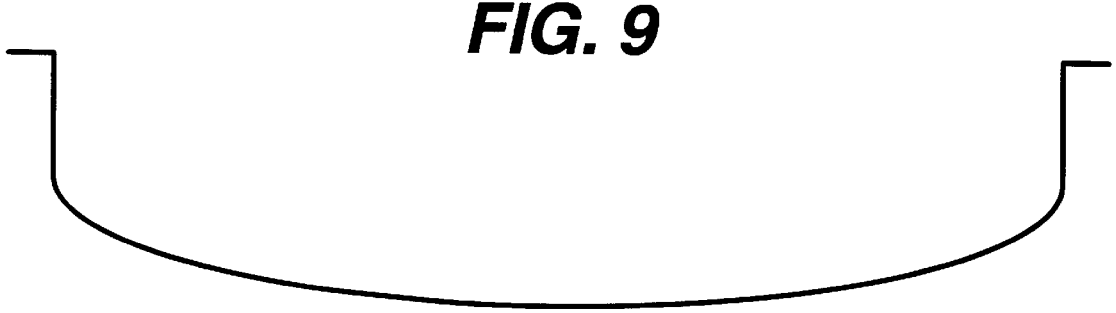
Figure 10:
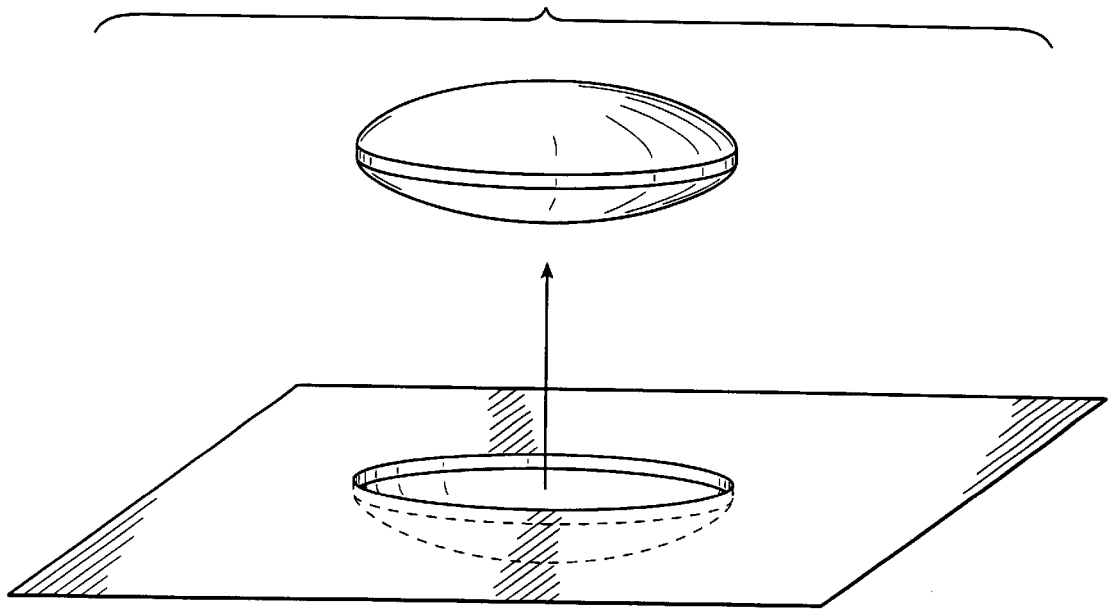
FIG. 10 shows the oval mold of FIG. 1 together with the corresponding biconvex solid dosage form obtainable therein.
Figure 11:
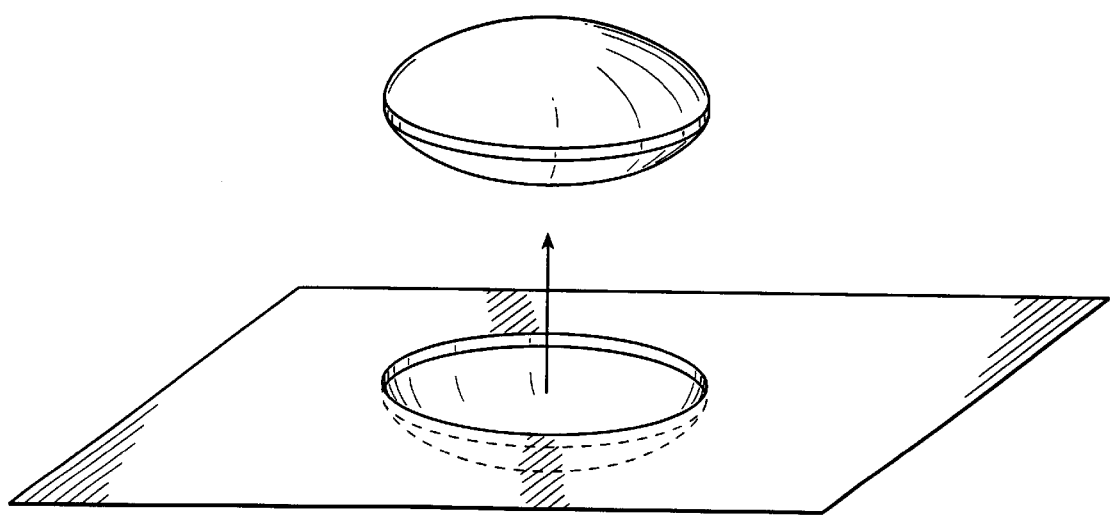
FIG. 11 shows a round mold together with the corresponding biconvex solid dosage form obtainable therein.

The square tablet is shown in FIG. 7, the oblate tablet in FIG. 4, the oval tablet in FIG. 1 and FIG. 10, and the round tablet in FIG. 11.

TABLE 1

| PARAMETER/SHAPE | SQUARE TABLET | OBLATE TABLET |
|---|---|---|
| $V_t$ = Volume$_{total}$ | 500 mm$^3$ | 1,000 mm$^3$ |
| $S_c$ = Surface$_{center}$ | length = 11 mm rounded corner r= 1.4 mm area = 119.8 mm$^2$ | length = 20 mm rounded ends r= 5 mm area = 178.54 mm$^2$ |
| $H_c$ = Height$_{center}$ | 2.00 mm | 2.70 mm |
| $H_m$ = Height$_{meniscus}$ | 1.80 mm (90%) | 2.20 mm (81.5%) |
| $H_t$ = Height$_{total}$ | 5.60 mm | 7.10 mm |
| Curve 1 | major = 11 mm minor = 3.6 mm | major = 20 min minor = 4.4 mm |
| Curve 2 | major = 14.4 mm minor = 3.6 mm | major = 10 mm minor = 4.4 mm |
| $V_c$ = Volume$_{center}$ = $S_c \times H_2$ | 239.6 mm$^3$ (47.9%) | 482.06 mm$^3$ (48.2%) |
| $V_m$ = Volume$_{meniscus}$ = $(V_t-V_c)/2$ | 130.2 mm$^3$ (26%) | 258.97 mm$^3$ (25.8%) |

| PARAMETER/SHAPE | OVAL TABLET | ROUND TABLET |
|---|---|---|
| $V_t$ = Volume$_{total}$ | 500 mm$^3$ | 1,000 mm$^3$ |
| $S_c$ = Surface$_{center}$ | length = 17 mm breadth = 9.3 mm area = 124.17 mm$^2$ | r = 8.4 mm area = 221.67 mm$^2$ |
| $H_c$ = Height$_{center}$ | 2.25 mm | 2.34 mm |
| $H_m$ = Height$_{meniscus}$ | 1.75 mm (77.8%) | 1.85 mm (79.1%) |
| $H_t$ = Height$_{total}$ | 5.75 mm | 6.53 mm |
| Curve 1 | major = 17mm minor = 3.5 mm | 16.8 mm 3.7 mm |
| Curve 2 | major = 9.3 mm minor = 3.5 mm | 16.8 mm 3.7 mm |
| $V_c$ = Volume$_{center}$ = $S_c \times H_2$ | 279.39 mm$^3$ (55.9%) | 518.71 mm$^3$ (51.2%) |
| $V_m$ = Volume$_{meniscus}$ = $(V_t-V_c)/2$ | 110.31 mm$^3$ (22.1%) | 240.65 mm$^3$ (24.1%) |

What is claimed is:

1. A process for the preparation of a solid rapidly disintegrating dosage form comprising a porous network of matrix forming materials, wherein said matrix forming materials comprise i) a water-soluble, hydratable gel or foam-forming material, ii) a rigidifying agent for the gel or foam-forming material and optionally iii) one or more amino acids and which process comprises:

overfilling a mold with a predetermined amount of an aqueous composition comprising the matrix forming materials so that a convex meniscus is created on top of the mold;

freezing the aqueous composition in the mold; and removing the solvent from the frozen composition by subjecting it to lyophilization or to solid state dissolution, thus leaving a porous network of matrix forming materials;

characterized in that the shape of the bottom surface of the mold is a mirror-image of the shape of the frozen meniscus on the top, the mirror-plane being parallel to the plane defined by the rim of the mold, thus yielding a dosage form shaped as a biconvex tablet having symmetrical top and bottom surfaces.

2. A process according to claim 1 wherein the volume of the mold is in the range of 300 to 2,000 mm3 (0.3 to 2 ml) and the volume of the dosage form is in the range of 350 to 2,500 mm3 (0.35 to 2.5 ml).

3. A process according to claim 2 wherein the volume of the mold is in the range of 350 to 800 mm3 (0.35 to 0.8 ml) and the volume of the dosage form is in the range of 450 to 1,000 mm3 (0.45 to 1 ml).

4. A process according to claim 1 wherein the maximum depth of the mold is in the range of 3.4 to 6 mm; or the maximum thickness of the frozen composition in the mold is in the range of 5.0 to 8.5 mm.

5. A process according to claim 1 wherein the area of the surface defined by the rim of the mold is in the range of 100 to 500 mm2 and has a rounded shape.

6. A process according to claim 5 wherein said rounded shape is circular, elliptical, oblong, oblate or polygonal, the latter with rounded corners if the internal angle$^2$ 90°.

7. A process according to claim 1 wherein the mold is a depression in a sheet of filmic plastic material or in a metal plate.

8. A process according to claim 7 wherein the mold is a thermoformed cup in a polypropylene sheet, the surface of which is optionally siliconized.

9. A process according to claim 1 wherein the aqueous composition is a solution, a suspension, a dispersion, an emulsion, or a foam.

10. A sheet made of filmic plastic material or of metal for use in the process of claim 1 which comprises a plurality of molds arranged in a regular pattern, characterized in that the shape of the bottom surface of each mold is a mirror-image of the shape of a predetermined convex meniscus on the top, the mirror-plane being parallel to the plane defined by the rim of the mold, the sheet thus being suitable for preparing dosage forms shaped as biconvex tablets having symmetrical top and bottom surfaces.

11. process according to claim 1 wherein the gel or foam forming material is selected from the group consisting of gelatin, gelatin A, gelatin B, fluid gelatin, modified fluid gelatin, gelatin derivatives, albumin, soy fiber protein, wheat, psyllium seed proteins, potato protein, papain, coacervate egg lecithin, lecithin, acacia, guar, agar, locust bean, xanthan, tragacanth gum, alginates, polymannuronic acid, chitosan, carrageenans, dextrans, dextrins, maltodextrins, pectins, polygalacturonic acid, microcrystalline cellulose, corn syrup solids, konjac flour, rice flour, wheat gluten, polyvinylpyrrolidone, sodium carboxymethyl-cellulose, sodium starch glycolate, hydroxyethylcellulose; and gelatin-acacia complexes, each singly or in combination.

12. A process according to claim 10 wherein the rigidifying material is selected from the group consisting of a mono-saccharide, a linear or cyclic oligosaccharide, a polysaccharide, an inorganic substance, and any combination thereof.

13. A process according to claim 12 wherein the rigidifying material is selected from the group consisting of mannitol, xylitol, sorbitol, dextrose, fructose, sucrose, lactose, maltose, galactose, trehalose, beta-cyclodextrin, 2-hydroxypropyl-beta-cyclodextrin, dextran, dextrin, sodium phosphate, sodium chloride, a magnesium aluminum silicate, magnesium trisilicate, and a natural clay, or any combination thereof.

14. A process according to claim 1 wherein the amino acid is glycine, L-aspartic acid, L-glutamic acid, L-hydroxyproline, L-isoleucine, L-phenylalanine, or a combination thereof.

15. A process according to claim 1 wherein the matrix forming materials comprise:

i) from 0.1% to 15% (w/w) of a water-soluble, hydratable gel or foam-forming material;

ii) from 0.5% to 10% (w/w) of a rigidifying agent for the gel or foam-forming material; and optionally;

iii) from 0.5% to 10% (w/w) of one or more amino acids.

16. A process according to claim 15 wherein the matrix forming materials comprise:

i) from 1.2% to 3% (w/w) of a water-soluble, hydratable gel or foam-forming material;

ii) from 1% to 4% (w/w) of a rigidifying agent for the gel or foam-forming material, and optionally;

iii) from 0.8% to 2.5% (w/w) of one or more amino acids.

17. A process according to claim 1 wherein the weight by weight ratio of the total amount of amino acids to that of the water-soluble, hydratable gel or foam-forming material is from 1:1 to 1:3; the weight by weight ratio of the amount of the water-soluble, hydratable gel or foam-forming material to that of the rigidifying agent is from 2:1 to 1:2; and the weight by weight ratio of the total amount of non-solvent components to that of the water in the aqueous composition ranges from 1:9 to 1:33.

18. A process according to claim 17 wherein the weight by weight ratio of the total amount of amino acids to that of the water-soluble, hydratable gel or foam-forming material is 1:1.5; the weight by weight ratio of the amount of the water-soluble, hydratable gel or foam-forming material to that of the rigidifying agent is 1.5:2; and the weight by weight ratio of the total amount of non-solvent components to that of the water in the aqueous composition ranges from 1:13 to 1:30.

19. A process according to claim 1 wherein the aqueous composition comprises a drug substance for human or veterinary use as an active ingredient.

20. A process according to claim 19 wherein the aqueous composition further comprises a substance selected from the group consisting of nutrients, vitamins, other active ingredients, sweeteners, flavouring agents, colouring agents, surfactants, preservatives, antioxidants, viscosity enhancers, minerals, diagnostics, fertilizers and insecticides.

21. A process according to claim 19 wherein the drug is cisapride [(±)-cis-4-amino-5-chloro-N-[1-[3-(4-fluorophenoxy)propyl]-3-methoxy-4-piperidinyl]-2-methoxy-benzamide monohydrate].

22. A process according to claim 1 wherein the matrix material can be disintegrated by water at 20° C. within 10 seconds.

23. A solid rapidly disintegrating dosage form obtainable by the process of claim 1.

* * * * *